United States Patent
Siegler

(10) Patent No.: US 7,361,474 B2
(45) Date of Patent: Apr. 22, 2008

(54) SERUM MACROPHAGE MIGRATION INHIBITORY FACTOR (MIF) AS MARKER FOR PROSTATE CANCER

(75) Inventor: Katherine Meyer Siegler, Seminole, FL (US)

(73) Assignee: United States of America as represented by The Department of Veterans Affairs, Washington, DC (US)

( * ) Notice: Subject to any disclaimer, the term of this patent is extended or adjusted under 35 U.S.C. 154(b) by 497 days.

(21) Appl. No.: 10/644,797

(22) Filed: Dec. 17, 2003

(65) Prior Publication Data

US 2004/0171021 A1    Sep. 2, 2004

Related U.S. Application Data

(60) Provisional application No. 60/448,894, filed on Feb. 24, 2003.

(51) Int. Cl.
  *G01N 33/53* (2006.01)
(52) U.S. Cl. .................. 435/7.1; 530/350; 530/388.23; 436/64
(58) Field of Classification Search ............... 435/7.23, 435/7.1; 530/350, 388.23, 388.24, 388.25, 530/388.8, 389.3, 389.7, 391.3; 436/64
See application file for complete search history.

(56) References Cited

U.S. PATENT DOCUMENTS

| | | | | |
|---|---|---|---|---|
| 5,250,297 | A | 10/1993 | Grauer et al. | .................. 424/88 |
| 5,614,372 | A | 3/1997 | Lilja et al. | .................. 435/7.23 |
| 5,654,161 | A | 8/1997 | Tewari | .................. 435/7.23 |
| 6,043,044 | A | 3/2000 | Hudson et al. | ............. 435/7.23 |
| 6,268,151 | B1 | 7/2001 | Murray et al. | .................. 435/6 |
| 6,420,188 | B1 | 7/2002 | Bucala et al. | ................ 436/500 |

OTHER PUBLICATIONS

Zhang et al. (Hepatobiliary Pancreat. Dis. Int. Nov. 2002; 1 (4): 577-580).*
Mitamura et al. (Br. J. Ophthalmol. 2000; 84: 636-639).*
Leech et al. (Arthritis Rheumatol. Apr. 2000; 43 (4): 827-833).*
Wright et al. (Prostate Cancer Prostatic Dis. Dec. 1999; 2 (5/6): 264-76).*
Meyer-Siegler et al. (Urology. 1996; 48: 448-452).*
Meyer-Siegler et al. (J. Interferon Cytokine Res. 2000; 20: 769-778).*
Koong et al. (Cancer Res. Feb. 15, 2000; 60: 883-887).*
Arcuri et al. (Prostate. 1999; 39: 159-165).*
Meyer-Siegler et al. (BMC Cancer. Jul. 6, 2005; 5 (1): 73; copy of electronically published document, pp. 1-12).*
Maaser et al. (Gastroenterology. Mar. 2002; 122 (3): 667-680).*
Meyer-Siegler et al. (Diagn. Mol. Pathol. Feb. 1998; 7 (1): 44-50).*
He et al. (Gut. 2006; 55: 797-802).*
Muramaki et al. (Oncol. Rep. 2006; 15: 253-257).*
Michael et al. (Prostate. 205; 62: 34-39).*
Kitaichi et al. (Graefe's Arch. Clin. Exp. Ophthalmol. 2006; 244: 825-828).*
Chen et al. (Am. J. Trop. Med. Hyg. 2006; 74 (1): 142-147).*
Kibiki et al. (Clin. Immunol. 2007; in press; copy of electronically published document, pp. 1-6).*
Rahman et al. (Annals Surg. Feb. 2007; 245 (2): 282-289).*
Yanagi et al. (Cytokine. 2006; 35: 270-274).*
Stephan et al. (Prostate. 2006; 66: 651-659).*
Vandenbroeck et al. 2003. Cytokine gene polymorphism in multifactorial diseases: gateways to novel targets for immunotherapy? TRENDS in Pharmacol. Sci. 24(6):284-289.
Meyer-Siegler et al. 2002. Macrophage migration inhibitory factor evaluation compared with prostate specific antigen as a biomarker in patients with prostate carcinoma. Cancer. 94(5):1449-1456.
Michael, Anja et al, "Serum Macrophage Migration Inhibitory Factor Is Not Elevated in Patients with Prostate Cancer". Cancer Epidemiology, Biomarkers & Prevention, vol. 13, pp. 328-329, Feb. 2004.
Li, Haojie et al, "Prediagnostic Plasma Vascular Endothelial Growth Factor Levels and Risk of Prostate Cancer". Cancer Epidemiology, Biomarkers & Prevention, Jun. 2005 vol. 14(6), pp. 1557-1561.
Yousef, G. M. et al, "Differential Expression of the Human Kallikrein Gene 14 (KLK14) in Normal and Cancerous Prostatic Issues". Prostate, Sep. 1, 2003 vol. 56(4), pp. 287-292.
Borgono, Carla A. "Human Kallikrein 14: A New Potential Biomarker for Ovarian and Breast Cancer". Cancer Research vol. 63, Dec. 15, 2003, pp. 9032-9041.

* cited by examiner

*Primary Examiner*—Stephen L. Rawlings
(74) *Attorney, Agent, or Firm*—Blank Rome LLP

(57) ABSTRACT

The present invention provides methods for detecting, diagnosing or prognosticating prostate cancer by measuring the levels of macrophage migration inhibitory factor (MIF) in the serum of an individual. The assay for MIF can be an immunoassay, such as ELISA, or a nucleic assay, such as Nouthern blot. Genetic changes within MIF gene can predict patients that express high levels of MIF.

11 Claims, 4 Drawing Sheets

SEQUENCE LISTING

<160> NUMBER OF SEQ ID NOS: 3

<210> SEQ ID NO 1
<211> LENGTH: 19

```
<212> TYPE: DNA
<213> ORGANISM: Homo sapiens

<400> SEQUENCE: 1
actaagaaag acccgaggc                                                  19

<210> SEQ ID NO 2
<211> LENGTH: 19
<212> TYPE: DNA
<213> ORGANISM: Homo sapiens

<400> SEQUENCE: 2
ggggcacgtt ggtgtttac                                                  19

<210> SEQ ID NO 3
<211> LENGTH: 11
<212> TYPE: PRT
<213> ORGANISM: Homo sapiens

<400> SEQUENCE: 3

Gly Ala Ala Lys Lys Gly Ala Val Gly Gly Ile
1               5                   10
```

SERUM MACROPHAGE MIGRATION INHIBITORY FACTOR (MIF) AS MARKER FOR PROSTATE CANCER

This application claims priority to U.S. Provisional Patent Application No. 60/448,894, filed Feb. 24, 2003.

FIELD OF THE INVENTION

The present invention relates to the diagnosis and prognosis of prostate cancer (CaP). More specifically, this invention uses the levels of macrophage migration inhibitory factor (MIF) in serum as a marker of CaP.

BACKGROUND OF THE INVENTION

Prostate cancer is the most common form of cancer among males. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S. In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, serum PSA concentrations do not always correlate well with the presence of prostate cancer, being positive in a percentage of non-prostate cancer cases, and serum PSA concentrations do not correlate with cancer severity.

Current clinical practice includes routine prostate cancer screening in men over the age of forty for prostate cancer. This screening involves looking for the protein prostate specific antigen (PSA) in the blood. This test does not always identify patients with prostate cancer and can't identify aggressive prostate cancer. Patients exhibit extreme variation in the progression of their prostate cancer. In some the cancer remains confined to the prostate and causes no harm to the patient. In others, the cancer spreads quickly throughout the body, especially to the bones. There are no accurate methods to determine the aggressiveness of prostate cancer. Therefore, the physician treating this disease does not have reliable ways to determine whether the prostate cancer will spread. The current treatments for prostate cancer often have significant negative effects on patient quality of life. This situation makes it difficult for the physician to make proper treatment decisions.

Using the technique of differential display polymerase chain reaction, it was found that the cytokine, macrophage migration inhibitory factor (MIF), is one gene whose expression is altered in metastatic prostate cancer when compared to normal tissue (Meyer-Siegler et al. (1996), *Urology* 48: 448-452).

MIF was first described thirty years ago and was designated as a cytokine, a chemical mediator, which regulates cell growth by inducing the expression of specific target genes. The initial described function of MIF was as a regulator of inflammation and immunity. It is expressed in the brain, and eye lens, is a delayed early response gene in fibroblasts, and it has been reported that this protein can be found in prostate tissues. MIF has been shown to be a pituitary, as well as macrophage cytokine and a critical mediator of septic shock. Recent studies also suggest that MIF may have an autocrine function for embryo development and is produced by the Leydig cells of the testes. Thus, it appears that this cytokine may play a fundamental role in cell growth regulation and possibly development.

U.S. Pat. No. 6,043,044 discloses the use of prostate tissue extracts as a patient sample to determine the amount of MIF. Immuno- and RNA blot analysis performed using homogenized tissue that contains variable proportions of epithelial and stromal cells still determined significant differences in the levels of MIF protein produced by metastatic tissue (490.3+/−71.3 ng/mg total protein). In practice this test was unreliable and difficult to perform because of contamination with surrounding connective and stromal tissue. It does not have utility in patient diagnosis or prognosis. Further, the patent does not mention or correlate serum MIF levels with prostate cancer. Therefore, a need exists for an improved assay with commercial application that is less invasive than that of the prior art.

SUMMARY OF THE INVENTION

This application describes a serum-based test for the diagnosis and prognosis of prostate cancer. It is more sensitive and reliable than the prior art. Since it is a serum-based test it does not require prostate biopsies. The biopsy process often does not recover useable tissue. In addition, the present invention uses serum samples from routine prostate specific antigen (PSA) screening tests; therefore, in patients undergoing prostate cancer screening this test, a separate biopsy of the prostate is not required. Thus, it more likely that patients will agree to be screened and monitored using this test.

The present invention provides methods for detecting or diagnosing or prognosticating prostate cancer. The methods comprise determining the levels of macrophage migration inhibitory factor (MIF) in an individual's serum.

The present invention further provides methods for monitoring the treatment of an individual with prostate cancer. The methods comprise administering a pharmaceutical composition to an individual and determining the levels of MIF in the individual's serum.

The present invention further provides methods for screening for an agent capable of modulating the onset or progression of prostate cancer. The methods comprise exposing an individual to the agent and determining the levels of MIF in the individual's serum.

In embodiments of the present invention, levels of serum MIF are determined by detecting MIF gene product in the serum using immunoassays or nucleic acid analysis, preferably mRNA. Gene products as recited herein can be nucleic acid (DNA or RNA) and/or proteins. In the case of DNA and RNA, detection occurs through hybridization with oligonucleotide probes. In the case of proteins, detection occurs though various protein interaction. Because MIF in serum is measured, the present invention provides a non-invasive blood test for prostate cancer.

The serum test of the present invention can be used alone or in conjunction with the commonly used PSA test. When used in conduction with the PSA test, patients at risk for prostate cancer would have elevated levels of both PSA and MIF; patients already diagnosed with prostate cancer with continued elevated levels of MIF in the blood, are likely to have more aggressive disease and would benefit from aggressive treatment.

DESCRIPTION OF THE PREFERRED EMBODIMENT

Figure 1:
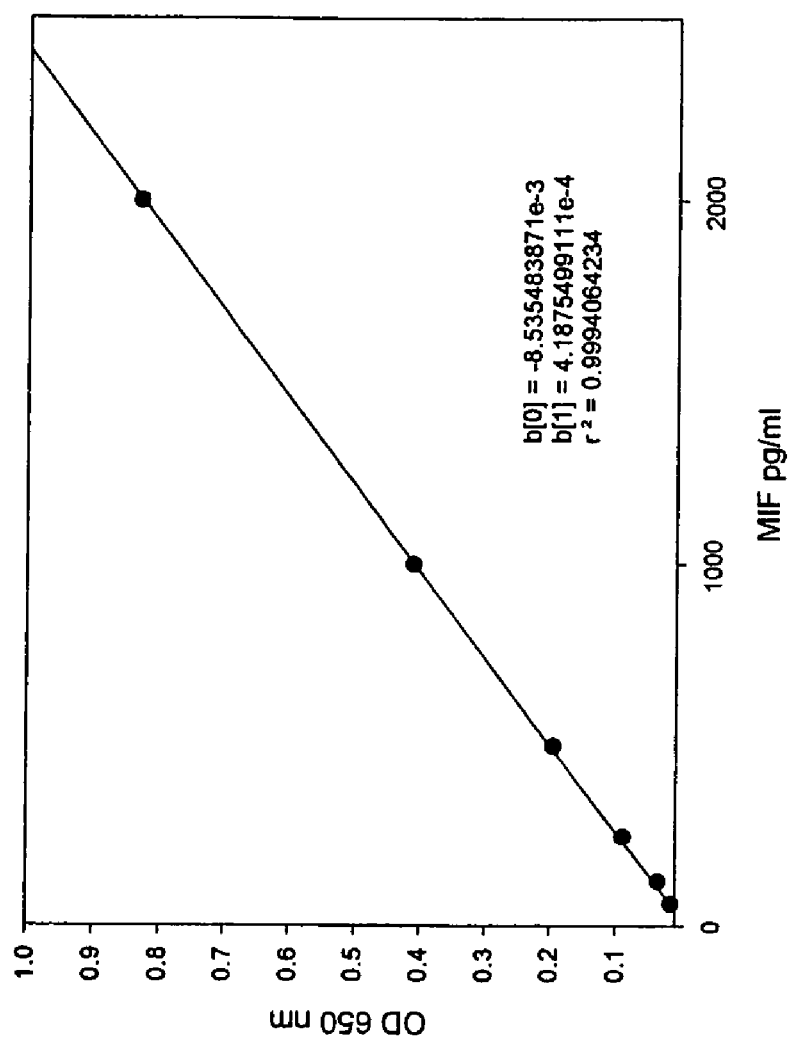
FIG. 1 shows a standard curve for the ELISA of Example 1.

Many biological functions are accomplished by altering the expression of various genes through transcriptional (e.g., through control of initiation, provision of RNA precursors, RNA processing, etc.) and/or translational control. For example, fundamental biological processes such as cell cycle, cell differentiation and cell death, are often characterized by the variations in the expression levels of individual gene or group of genes.

Changes in gene expression also are associated with pathogenesis. For example, the lack of sufficient expression of functional tumor suppressor genes and/or the over expression of oncogene/protooncogenes could lead to tumorgenesis or hyperplastic growth of cells (Marshall (1991) *Cell* 64:313-326; Weirlberg (1991), *Science* 254:1138-1146). Thus, changes in the expression levels of particular gene or group of genes (e.g., oncogenes or tumor suppressors) serve as signposts for the presence and progression of various diseases.

Monitoring changes in gene expression may also provide certain advantages during drug screening development. Often drugs are screened and prescreened for the ability to interact with a major target without regard to other effects the drugs have on cells. Often such other effects cause toxicity in the whole animal, which prevent the development and use of the potential drug.

The present inventor have identified serum MIF as a gene marker associated with prostate. Changes in serum MIF can also provide useful markers for diagnostic uses as well as markers that can be used to monitor disease states, disease progression, drug toxicity, drug efficacy and drug metabolism. The present inventor have also identified a genetic polymorphism in the MIF gene associated with prostate cancer.

Use of Serum MIF as Diagnostics

As described herein, the serum MIF may be used as diagnostic markers for the prediction or identification of prostate cancer. For instance, a serum sample from a patient may be assayed by any of the methods described herein or by any other method known to those skilled in the art, and the expression levels MIF may be compared to the expression levels found in normal serum. The serum expression levels of MIF that substantially resemble an expression level from the serum of normal or of diseased prostate may be used, for instance, to aid in disease diagnosis and/or prognosis. Comparison of the serum MIF levels may be done by researcher or diagnostician or may be done with the aid of a computer and databases. Preferably, the present method involves comparing the levels of MIF in the serum of the individual to the MIF levels of prostate cancer patients.

Serum MIF levels of greater than about 5 to about 10 ng/ml, most preferably greater than about 6 ng/ml, indicates the presence of prostate cancer. Serum MIF levels can also be used in conjunction with the commonly used PSA test to accurately detect the presence of prostate cancer.

Use of Serum MIF for Drug Screening

According to the present invention, serum MIF levels may be used as markers to evaluate the effects of a candidate drug or agent on a prostate cancer patient.

A patient is treated with a drug candidate and the progression of prostate cancer is monitored over time. This method comprises treating the patient with an agent, obtaining a serum sample from the patient, determining levels of MIF in the serum, and comparing the levels of MIF over time to determine the effect of the agent on the progression of prostate cancer.

The candidate drugs or agents of the present invention can be, but are not limited to, peptides, small molecules, vitamin derivatives, as well as carbohydrates. Dominant negative proteins, DNA encoding these proteins, antibodies to these proteins, peptide fragments of these proteins or mimics of these proteins may be introduced into the patient to affect function. "Mimic" as used herein refers to the modification of a region or several regions of a peptide molecule to provide a structure chemically different from the parent peptide but topographically and functionally similar to the parent peptide (see Grant (1995), in *Molecular Biology and Biotechnology*, Meyers (editor) VCH Publishers). A skilled artisan can readily recognize that there is no limit as to the structural nature of the candidate drugs or agents of the present invention.

Use of Serum MIF for Monitoring Disease Progression

As described above, the expression of serum MIF may also be used as markers for the monitoring of disease progression, for instance, the development of prostate cancer. For instance, a serum sample from a patient may be assayed by any of the methods described above, and the expression levels in the sample of MIF may be compared to the expression levels found in normal serum. The MIF in serum can be monitored over time to track progression of the disease. Comparison of the serum MIF levels may be done by researcher or diagnostician or may be done with the aid of a computer and databases.

Assay Formats

The over expression of MIF is manifest at both the level of messenger ribonucleic acid (mRNA) and protein. It has been found that increased serum MIF, determined by either mRNA levels or biochemical measurement of protein levels using immunoassays, is associated with prostate cancer.

In an embodiment of the present invention, serum MIF levels are detected by immunoassays. Generally, immunoassays involve the binding of the MIF and anti-MIF antibody. The presence and amount of binding indicate the presence and amount of MIF present in the sample. Examples of immunoassays include, but are not limited to, protein arrays, ELISAs, radioimmunoassays, and immunoblots, which are well known in the art. The antibody can be polyclonal or monoclonal and is preferably labeled for easy detection. The labels can be, but are not limited to biotin, fluorescent molecules, radioactive molecules, chromogenic substrates, chemi-luminescence, and enzymes.

In a preferred embodiment, ELISA, based on the capture of MIF by immobilized monoclonal anti-MIF antibody followed by detection with biotinylated polyclonal anti-MIF antibody, is used to detect serum MIF. In this system, the wells of a multi-well plate are coated with the monoclonal antibody and blocked with milk (albumin blocking should be avoided because MIF has been shown to bind albumin). Serum samples are then added to the wells and incubated for capture of MIF by the monoclonal antibody. The plate is then detected with the polyclonal antibody and strepavidine-alkaline phosphatase conjugate.

In another embodiment, serum MIF levels are detected by measuring nucleic acid levels in the serum, preferably MIF mRNA. This is accomplished by hybridizing the nucleic acid in the serum with oligonucleotide probes that is specific for the MIF gene.

Nucleic acid samples used in the methods and assays of the present invention may be prepared by any available method or process. Methods of isolating total RNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I—Theory and Nucleic Acid Preparation, Tijssen, (1993) (editor) Elsevier Press. Such samples include RNA samples, but also include cDNA synthesized from a mRNA sample isolated from a cell or tissue of interest. Such samples also include DNA amplified from the cDNA, and an RNA transcribed from the amplified DNA. One of skill in the art would appreciate that it is desirable to inhibit or destroy RNase present in homogenates before homogenates can be used.

Nucleic acid hybridization simply involves contacting a probe and target nucleic acid under conditions where the probe and its complementary target can form stable hybrid duplexes through complementary base pairing (see U.S. Pat. No. 6,333,155 to Lockhart et al, which is incorporated herein by reference). Methods of nucleic acid hybridization are well known in the art. In a preferred embodiment, the probes are immobilized on solid supports such as beads, microarrays, or gene chips.

The hybridized nucleic acids are typically detected by detecting one or more labels attached to the sample nucleic acids and or the probes. The labels may be incorporated by any of a number of means well known to those of skill in the art (see U.S. Pat. No. 6,333,155 to Lockhart et al, which is incorporated herein by reference). Commonly employed labels include, but are not limited to, biotin, fluorescent molecules, radioactive molecules, chromogenic substrates, chemiluminescent labels, enzymes, and the like. The methods for biotinylating nucleic acids are well known in the art, as are methods for introducing fluorescent molecules and radioactive molecules into oligonucleotides and nucleotides.

Detection methods, for both the immunoassays and the nucleic acid assays, are well known for fluorescent, radioactive, chemiluminescent, chromogenic labels, as well as other commonly used labels. Briefly, fluorescent labels can be identified and quantified most directly by their absorption and fluorescence emission wavelengths and intensity. A microscope/camera setup using a light source of the appropriate wavelength is a convenient means for detecting fluorescent label. Radioactive labels may be visualized by standard autoradiography, phosphor image analysis or CCD detector. Other detection systems are available and known in the art.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

EXAMPLE 1

ELISA

A MIF-specific ELISA assay was developed, based on the capture of MIF by immobilized monoclonal anti-MIF antibody followed by detection with goat polyclonal anti-MIF affinity purified IgG. This assay was performed as follows:

1. ELISA plate wells were coated with 2 µg/ml monoclonal antibody in PBS (100 µl/well); immediately following preparation of working monoclonal antibody (MAb) solution 100 µl aliquots of working antibody solution are transferred to each well of an ELISA plate. Plates are sealed and incubated overnight at 4° C.
2. ELISA plate wells are washed. This process involves "flipping" the contents of the plate into a sink and rapping the plate three times on a wad of paper towels placed on top of a folded towel. Wells were the washed by filling the wells individually with wash buffer using a squeeze bottle, followed by removal of contents by "flipping" and drying on paper towels. The wash process is repeated for a total of four washes. At the end of the last wash the plate was inverted on the paper towel for 1 minute to allow any remaining wash buffer to drain.
3. Wells were then blocked with a 1:20 dilution of milk diluent (50-82-01, Kirkegaard and Perry) for 1hour at room temperature (Plates were placed inside a drawer to prevent temperature fluctuations). Avoid use of blocking agents that contain albumin. MIF has been shown to bind to albumin and an albumin like molecule called sarcolectin.
4. Plates were washed as described in step 2.
5. MIF standards were prepared in 1.5 ml polypropylene microfuge tubes by adding 500 µl milk diluent and running doubling dilutions. Serum samples were likewise diluted if necessary. Because hemolyzed serum samples contains artificially elevated MIF concentrations, its use should be avoid.
6. Samples and standards were applied to the plate (100 µl/well) and the plate sealed and incubated overnight at 4° C. with gentle shaking.
7. The plate was then washed as described in step 2 and second antibody (BAF289, R&D Systems) added at 100 µl/well. The optimal dilution of this antibody must be determined empirically each time a new aliquot is used. Any variation in the standard curve was usually due to degradation of this reagent.
8. The plate was sealed and incubated 2 hours at room temperature with gentle shaking.
9. All wells were then washed five times as in step 2 and the strepavidin-alkaline phosphatase conjugate (the optimal dilution of this reagent was also determined empirically, but was usually 1: 1000) was added at 100 µl/well.
10. The plate was covered, incubated for 35 minutes at room temperature, and then washed 5 times as in step 2.
11. The wells were then developed with BluPhos™ (Kirkegaard and Perry Laboratories, Gaithersburg, Md.). Reaction product was allowed to develop in the dark at room temperature, and read at 630 nm within 15-30 minutes.

This assay gives range of sensitivity of about 50 pg/ml-1.5 ng/ml. FIG. 1 shows the standard curve for the assay. It should be noted that for the practice of this ELISA, various combinations of two or more MIF-specific antibodies could be used to capture and detect MIF in a sample.

EXAMPLE 2

Serum MIF and Prostate Pathology

Four pathological groups were defined: benign prostatic hyperplasia (BPH), CaP, high-grade prostate intraepithelial neoplasia (HGPIN), and none available (patients without listed diagnosis or prostate pathology report). The mean serum MIF was determined for each group and is summarized in the following table:

TABLE 1

Serum MIF and Prostate Pathology

| Prostate pathology | Sample size (n) | Serum MIF (mean ± SE) |
|---|---|---|
| None available | 357 | 1.9 ± 0.28 |
| Benign prostatic hyperplasia | 84 | 2.7 ± 0.58 |
| CaP | 61 | 6.8 ± 0.87 |
| High grade PIN | 7 | 10.1 ± 3.35 |

Using serum from patients tested for thyroid stimulating hormone concentrations (n=14) as a control a pair wise Dunn's multiple comparison test of Krudkal-Wallis ANOVA on ranks identified significant difference in serum MIF levels between the control and high grade PIN, as well as control and CaP (P<0.001). These data suggest a correlation between CaP and elevated serum MIF.

Serum MIF concentrations were found not to correlate with prostate tumor TMN classification (ANOVA, P=0.116; this may be attributed to the small sample size available for the study). However, ANOVA of this same CaP cohort stratified according to Gleason score (G≦4, G5/6, G≧7) determined a significant difference (P=0.012) in mean serum MIF concentrations. Dunn's pair wise comparison determined significant increase (P<0.05) in serum MIF concentrations in the G5/6 and G≧7 when compared with G≦4. As seen in the following table these data indicate that increased serum MIF concentrations are associated with higher Gleason score tumors.

TABLE 2

CaP Pathology Correlated to Serum MIF and PSA

| Gleason Score | Sample size (%) | Serum PSA (mean ng/ml) | Serum MIF (mean ng/ml) |
|---|---|---|---|
| ≦4 | 16 (26.2) | 3.23 ± 2.11 | 2.13 ± 0.73 |
| 5 or 6 | 24 (39.3) | 3.78 ± 1.20 | 6.44 ± 0.51 |
| ≧7 | 21 (34.4) | 4.49 ± 1.59 | 8.67 ± 1.34 |

Figure 2:
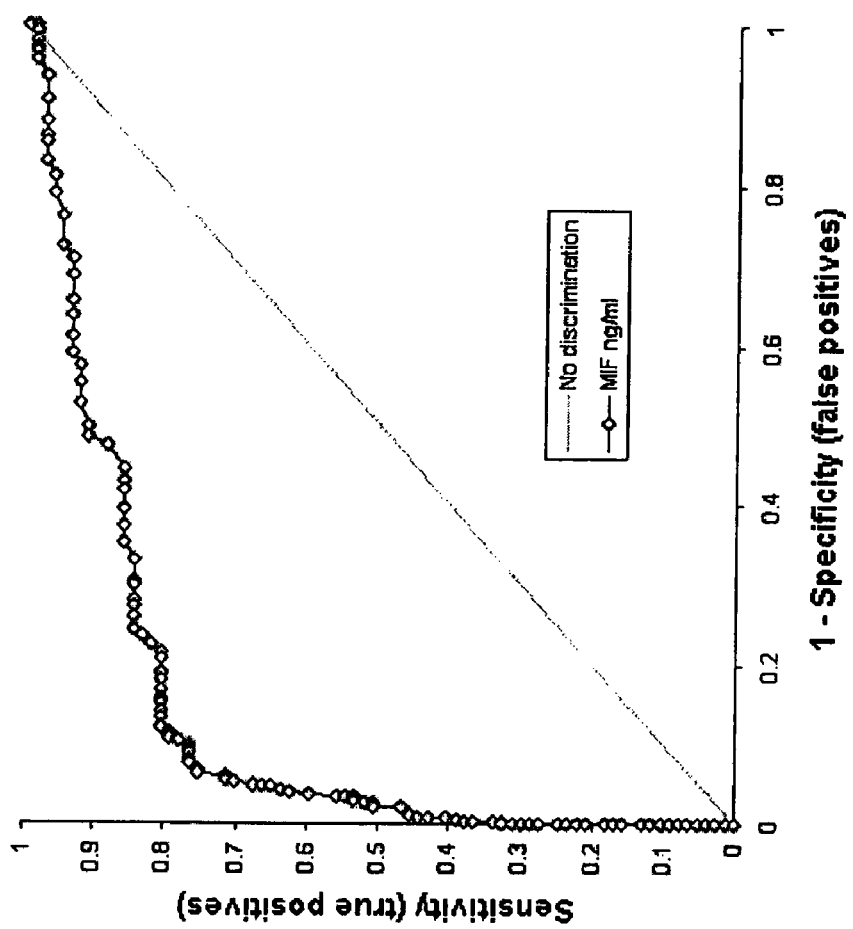
FIG. 2 shows a MIF ROC analysis.

Receiver Operating Characteristic Curves (ROC) are a standard statistical method used in the evaluation of a biomarker in disease diagnosis. This analysis determines the ability of a test to discriminate diseased cases from normal cases. The value of the area under the ROC curve is a measure of test accuracy. A ROC analysis of 460 patients (383 normal and 77 CaP patients) identified the area under the curve as 87.5% indicating that serum MIF is predictive of prostate cancer (P<0.0001) (see FIG. 2). The 95% confidence interval (0.821 to 0.929) indicates that serum MIF does have the ability to distinguish prostate cancer patients from normals.

Disease (CaP) presence was defined as the prostate cancer patients with positive biopsy (n=77, mean MIF 10.82 ng/ml, mean PSA 5.5 ng/ml). Disease CaP absence was defined as patients with no documented prostate pathology. These were the patients that were not included in the original analysis (n=383, mean MIF 3.46 ng/ml, mean PSA 1.79 ng/ml).

EXAMPLE 3

Detection of MIF Protein in Prostate Tissue

Previous experiments identified MIF as being localized within prostate epithelial cells (Meyer-Siegler (1998), *Diagnostic and Molecular Path.* 7: 44-50). Analysis of MIF staining within prostate tissue using the biopsy samples (same as used for serum analysis, Table 2) demonstrated an association between MIF immunoperoxidase staining and prostate tumor Gleason score (n=61, P<0.001). Interestingly, Gleason score 5 or 6 tumors (n=24) exhibit intense MIF immunoperoxidase staining. The diffuse staining distribution is found in the cytoplasm around the nucleus. While, G≧7 tumors exhibit little positive immunostaining (n=21), suggesting that higher Gleason score tumor cells contain less intracellular MIF protein. The IHC results along with the results of the serum study suggest that G≧7 tumors exhibit enhanced MIF secretion. The results of a similar study by another laboratory demonstrated that with histological dedifferentiation, prostate adenocarcinoma cells exhibit altered MIF protein concentration (Arcuri et al. (1999), *Prostate* 39: 159-165). These authors suggest that this finding may be the consequence of changes in MIF synthesis or the result of an enhanced and/or altered secretion by tumor cells into the surrounding stroma (Arcuri et al.). Interestingly, the aforementioned study did not find significantly reduced intracellular MIF concentration in prostate tumor cells after patients underwent combined endocrine treatment (Arcuri et al.). These results and those showing elevated serum MIF in some CaP patients who have undergone endocrine treatment, which has reduced serum PSA to normal levels, seems to exclude androgen regulation of MIF secretion in the prostate (Arcuri et al.; Meyer-Siegler et al. (2002), *Cancer* 94:1449-56). Additional studies of lung adenocarcinoma patients determined a strong association between poor prognosis and increased MIF IHC staining intensity (Kayser et al. (1998), *Anal. Quant. Cytol. Histol.* 20:313-320), further supporting the role of MIF in tumor aggressiveness.

EXAMPLE 4

Detection of MIF mRNA in Prostate Tissue

Previous experiments documented that in vitro cultured prostate cells express MIF mRNA and that MIF message amounts are significantly higher in CaP cell lines (Meyer-Siegler (2000b), *Cytokine* 12: 914-921). However, increased MIF mRNA expression within CaP epithelial cells has not been documented in vivo. To associate altered serum MIF with MIF mRNA expression, laser capture microscopy (LCM) of prostate epithelial cells was used to determine MIF mRNA amounts by Q-RT-PCR. Expression analysis of LCM dissected cells excludes mRNA that may be contributed by stromal or immune cells. These studies examined MIF expression in glandular epithelial cells. MIF mRNA amounts, normalized to 18S rRNA, are higher in the cells invasive to the margin when compared with normal and focal cancer cells from the same biopsy. Arbitrary MIF mRNA expression ratios (MIF area-intensity/18S rRNA area-intensity) for each tissue category (normal, CaP, invasive to margin) from 3 separate Q-RT-PCR analyses of 3 different patients (all with stage pT3b tumors) were analyzed by ANOVA. ANOVA defined significant differences (P<0.001) between normal prostate epithelial cell MIF expression ratios (0.38±0.06), focal CaP MIF expression ratios (1.88±0.12) and invasive CaP expression ratios (2.48±0.23). Tukey pair wise multiple comparisons determined that MIF expression ratios were significantly higher (P<0.05) in CaP and invasive CaP prostate epithelial cells when compared with normal epithelial cells from the same biopsy. Negative controls (RNA-free water) did not show any amplified product, nor was a band visible following direct amplification of purified genomic DNA (Meyer-Siegler et al. (2002)). These results indicate that the increased serum MIF detected in patients with CaP may be due, in part, to increased MIF gene expression in CaP epithelial cells. These results document elevated in vivo MIF mRNA expression in CaP.

EXAMPLE 5

Elevated serum MIF is Associated with PSA Failure

The association between increased serum MIF (>6 ng/ml) and PSA failure at 6 months and 12 months following study initiation was determined. The prognosis of CaP patients is strongly related to increases in serum PSA (PSA failure). PSA failure (defined in this study as a minimum 0.5 ng/ml rise in PSA over 6 months) is often used as an earlier indicator of prostate cancer "relapse". The aim of this feasibility study was to evaluate serum MIF in predicting CaP prognosis by assessing its association with PSA failure in a veteran CaP population. Computerized Patient Record System (CPRS) was used to search the CaP cohort identified in the initial study to determine subsequent PSA determinations for this cohort at 6 months and 12 months following initiation into the study. Associations between PSA failure and initial MIF concentration were determined by Fisher exact test. The record search identified 67 CaP patients with documented PSA at 6 and 12 months following the serum MIF determination at study initiation. Mean PSA values were calculated for CaP cohort groups 1-4 [determined by serum concentrations of PSA (low<4 ng/ml versus high>4 ng/ml) and MIF (low<6 ng/ml versus high>6 ng/ml) at study initiation]. The data are described in the following table:

TABLE 3

Change in Mean PSA in CaP patients Stratified according to MIF/PSA

| Group | Description | n | MIF study initiation | PSA study initiation | PSA 6 months | PSA 12 months |
|---|---|---|---|---|---|---|
| 1 | Low PSA/Low MIF | 15 | 3.15 ± 0.42 | 0.87 ± 0.15 | 0.86 ± 0.72 | 1.23 ± 1.17 |
| 2 | High PSA/Low MIF | 2 | 1.30 ± 0.25 | 7.05 ± 1.95 | 5.35 ± 3.65 | 6.85 ± 1.85 |
| 3 | Low PSA/High MIF | 38 | 13.06 ± 2.09 | 1.27 ± 0.20 | 1.17 ± 0.24 | 2.22 ± 0.36 |
| 4 | High PSA/High MIF | 12 | 11.91 ± 1.38 | 11.03 ± 2.02 | 4.47 ± 1.38 | 5.78 ± 1.38 |

Data is expressed as mean± standard error. ANOVA of PSA values at study entry, 6 months and 12 months was used to determine significant differences in mean PSA values among the groups. In all instances significant differences were found (P<0.001) However, Tukey pairwise multiple comparisons determined a significant difference only between groups 1&4 and 3&4 (P<0.05). These data did not determine a significant difference between mean PSA between groups 1&3, which would be expected if elevated serum MIF concentrations were independently predictive of CaP relapse. Since the patients in this CaP cohort were undergoing various treatment modalities, which alter serum PSA we determined the association between serum MIF concentration at study initiation and rise in serum PSA (0.5 ng/ml or greater over 6 month intervals). ANOVA comparing the change in PSA over time (0, 6 and 12 months) in patients with low PSA determined a significant difference in mean PSA between groups 1 &3, P=0.033. Tukey pairwise multiple comparisons determined a significant difference between the PSA values of the two groups at 12 months (P<0.05). These data indicate that an increase in serum PSA is associated with an initial high serum MIF concentration.

EXAMPLE 6

PSA Rise Versus Time Since Study Initiation in CaP Patients With High and Low Serum MIF Patients (n=67) in the CaP cohort were divided into Low MIF (<6 ng/ml, n=17) and High MIF (>6 ng/ml, n=50) groups independent of PSA concentration, based upon the serum MIF concentration at study initiation. The number of patients exhibiting a 0.5 ng/ml rise in PSA at 6 months and 12 months following study initiation were determined.

TABLE 4

Number Patients with Rising PSA

| Months | Low MIF n = 17 | | High MIF n = 50 | |
|---|---|---|---|---|
| | # with rising PSA | Percentage | # with rising PSA | Percentage |
| 6 | 2 | 11.8 | 5 | 10.0 |
| 12 | 5 | 29.4 | 30 | 60.0 |

Using a 0.5 ng/ml rise in PSA as an outcome, a significant (30.6%) increase in PSA failure was determined in CaP patients with high serum MIF at study initiation. Fisher's exact test determined a significant difference in the number of patients with rising PSA in the low MIF versus high MIF groups (P=0.048). Elevated serum MIF (>6ng/ml) is predictive of disease progression using 0.5 ng/ml rise in PSA over 6 month intervals as the disease progression criteria. It is feasible to use serum MIF concentrations as a strategy to determine risk of biochemical progression with time. Thus, this may be a tool to differentiate patients with indolent disease from those with biologically active disease.

EXAMPLE 7

MIF Single Nucleotide Polymorphism (SNP) Identified in Aggressive CaP Cell Lines Previous data established an increase in MIF transcription in aggressive CaP cells (Meyer-Siegler (2000a), *J. Interferon and Cytokine Res.* 20(9): 769-778). At the time a molecular mechanism for the increased MIF mRNA concentrations was not known. A recent publication associated a MIF SNP in the MIF promoter region with systemic juvenile arthritis (Donn et al.(2001), *Arthritis and Rheum.* 44: 1782- 1785) and the creation of an AP-4 transcription factor-binding site. The presence of an additional transcription factor binding site results in increased MIF gene expression and could therefore be associated with prostate tumor aggressiveness. Analysis of this region in normal, BPH-1, LNCaP, C4-2b, DU-145 and PC-3 cells was undertaken. Genomic DNA was isolated from cells and 0.1 µg of DNA amplified by PCR with the following primers 5'ACTAAGAAAGACCCGAGGC3' (SEQ ID NO: 1) and 5'GGGGCACGTTGGTGTTTAC3' (SEQ ID NO: 2) for 30 cycles of 95° C. for 1 min, 60° C. for 1 min and 72° C. for 1 min. The resulting 366 bp PCR products were purified and 1 µg of PCR product digested with 3U Alu I overnight. Resulting restriction digests were separated by agarose electrophoresis and photographed. This SNP is present in the more aggressive CaP cell lines (C4-2b, DU-145 and PC-3), but absent from normal and the less aggressive LNCaP cell line. GenBank™ analysis determined the presence of an expressed sequence tag for AP-4 in the prostate (A 1669905). These data suggest that the MIF polymorphism is associated with a positive role in gene expression and provide additional evidence of a functional SNP in the 3' regulator region of the gene. This is a potential genetic mechanism to explain the increased MIF expression seen in aggressive Gleason score tumors (Meyer-Siegler et al. (2002)) and CaP cell lines (Meyer-Siegler (2000a); Meyer-Siegler (2000b); Meyer-Siegler (2001), *Molec. Med.* 7: 850-860).

EXAMPLE 8

MIF Prostate Protein Complex Identification

Figure 3:
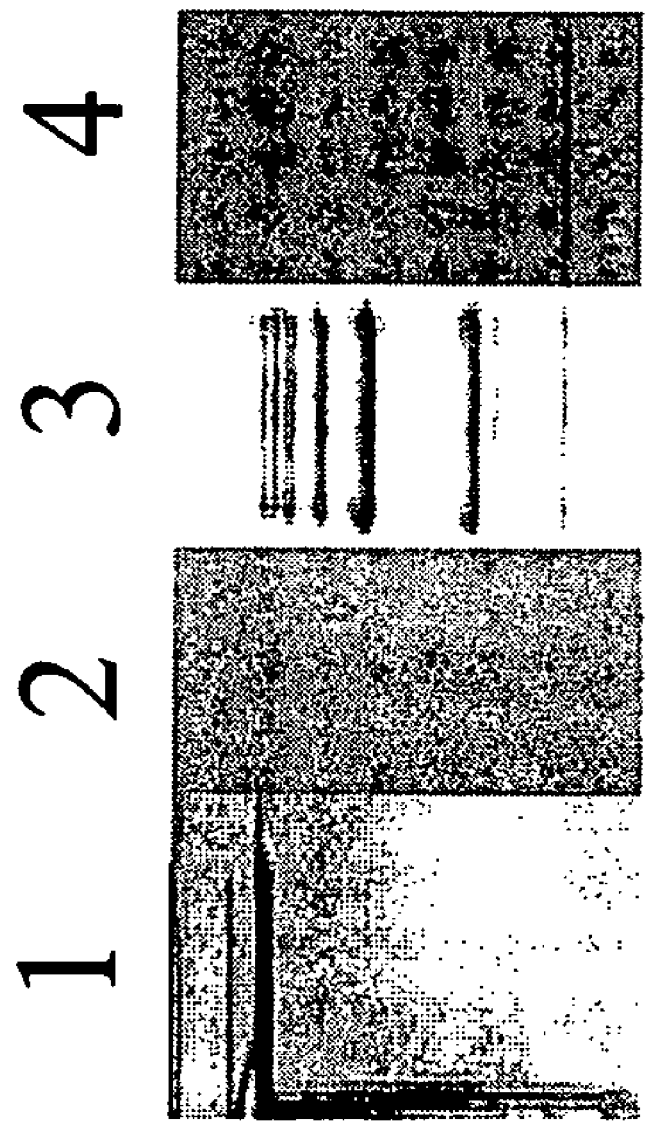
FIG. 3 shows the MIF prostate protein complex. LNCaP MIF antibody affinity purified cell lysate separated by non-reducing PAGE resulted in high MW band (lane 1) that was immunoreactive with MIF polyclonal antibody (lane 2). Treatment of lysate with reducing agents revealed multiple proteins on SDS-PAGE gels (lane 3), only one of which was immunoreactive with MIF polyclonal antibody (lane 4).

Studies to determine MIF's intracellular nature identified a multi-protein complex. LNCaP prostate cancer cells ($5\times10^6$) were lysed (10 mM CHAPS, 2mM EDTA, 4mM iodoacetate in PBS pH 7.2 with protease inhibitor cocktail); cell debris pelleted and cleared lysate applied to MIF polyclonal antibody (R&D Systems, Minneapolis, Minn.) affinity column. Antibody purified fractions were concentrated 10-fold (YM-3 Centricon), and analyzed by non-reducing PAGE, which identified a high MW band (178 kDa) recognized by MIF polyclonal (FIG. 3, lane 2), but not MIF monoclonal antibody (R&D Systems). MIF forms oligomers (Sun et.al. (1996), *Protein Engineering* 9: 631-635), so the original thought was that this was an oligomeric MIF form. However, reducing SDS-PAGE identified a multi-protein complex with only one 12 kDa band recognized by both MIF antibodies (FIG. 3, lane 4 polyclonal Ab).

MALDI-TOF mass spectroscopy and Edman degradation tryptic peptide sequence analysis was used to identify components of this novel protein complex. The complex proteins are N-terminal blocked, precluding less expensive protein sequencing from PVDF membranes. One protein identified is A20, a cytokine-inducible zinc finger protein, which regulates NF-κβ activity (Heyninck and Beyaert (1999), *FEBS Lett.* 442: 147-150). Another is an unknown 70-kDa protein with a peptide sequence GAAKKGAVGGI (SEQ ID NO: 3). SwissPro™ database search, revealed no known homologus protein sequences to the unknown protein peptide. A third component of this complex has been identified as human glandular kallikrein-2 (hK2). These new data support those of a previous study, which documented the association of MIF and hK2 in experiments designed to purify hK2 from human seminal fluid (Meinhardt et.al. (1999), *J. Cell Sci.* 112:1337-1344). Kallikrein gene family proteins are serine proteases (Yousef and Diamandis (2001), *Endocr Rev.* 22: 184-204). In the human prostate the KLK3 kallikrein gene encodes PSA (aka human kallikrein 3, hK3) (Riegman et al. (1992), *Genomics* 14:6-11). hK2 has trypsin like activity and can activate the pro-form of PSA to its active form (Kumar et.al. (1997), *Cancer Res.* 57:3111-3114). Expression of KLK2, the gene encoding the hK2 protein, is up-regulated in prostate carcinoma (Darson et.al. (1997), *Urology* 49:857-862). hK2 may participate in prostate growth factor and cytokine networks (Rittenhouse et.al. (1998), *Crit. Rev. Clin. Lab. Sci.* 35:275-368). These data are intriguing given the established interaction between PSA and hK2 and the latter's apparent interaction with cytokines, such as MIF. A20 identity in the MIF complex was confirmed by coimmunoprecipitation pull down experiments.

Figure 4:
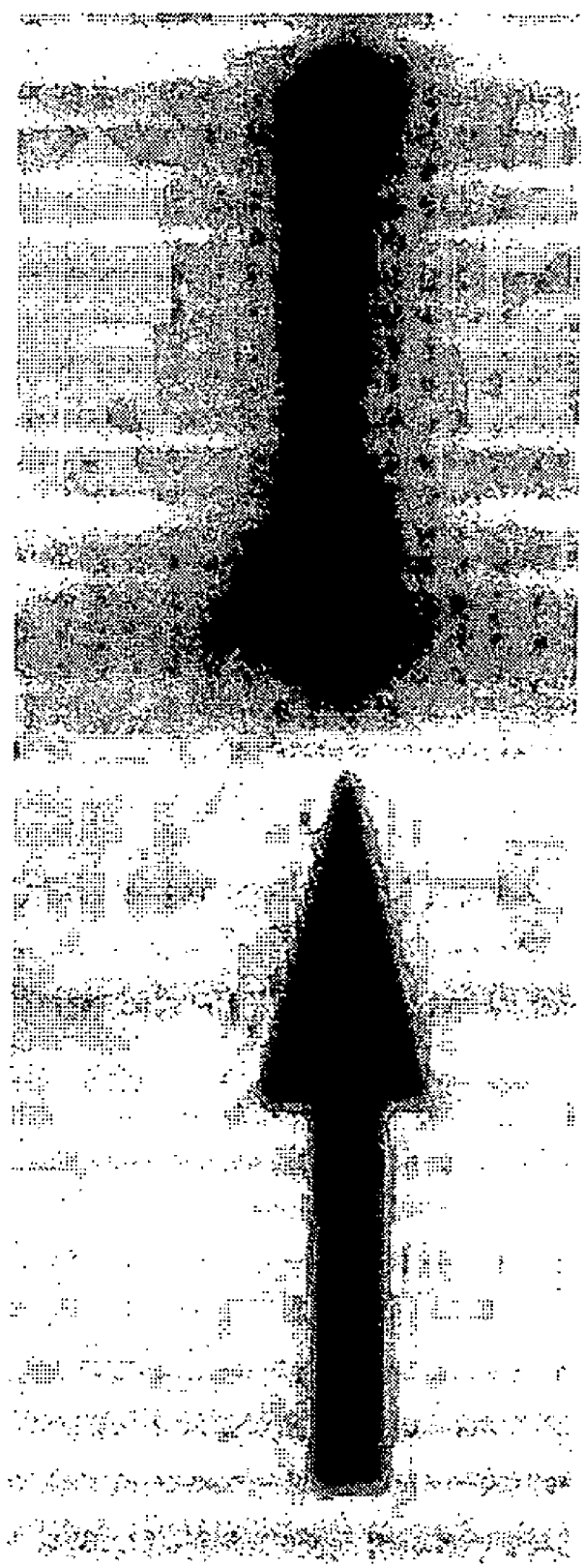
FIG. 4 shows MIF identified by immunoprecipitation with A20 monoclonal antibody.

A20 monoclonal antibody (from Dr. Vincenz, University of Michigan) was used to immunoprecipitate A20 protein from LNCaP cell lysates. The resulting protein was subjected to Western blot analysis using reducing SDS-PAGE and MIF monoclonal antibody identifying a 12 kDa MIF band (FIG. 4).

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for detecting or diagnosing prostate cancer in an individual comprising the step of determining levels of macrophage migration inhibitory factor (MIF) and prostate specific antigen (PSA) in the serum of the individual; and detecting or diagnosing prostate cancer where the serum MIF levels are greater than about 5 to about 10 ng/ml and the PSA levels are elevated, as compared to PSA levels in serum from normal, unaffected individuals.

2. The method of claim 1, wherein the determining step is accomplished by immunoassay.

3. The method of claim 2, wherein the immunoassay is an ELISA.

4. The method of claim 2, wherein the immunoassay is an immunoblot.

5. The method of claim 2, wherein the immunoassay is a protein array.

6. The method of claim 1, wherein the determining step comprises the steps of contacting the serum of the individual with a molecule that specifically binds MIF; and detecting the presence of binding between MIF and the molecule.

7. The method of claim 6, wherein the molecule is an antibody.

8. The method of claim 7, wherein the antibody is selected from the group consisting of monoclonal antibodies and polyclonal antibodies.

9. The method of claim 6, wherein the molecule is labeled.

10. The method of claim 9, wherein the label is selected from the group consisting of biotin, fluorescent molecules, radioactive molecules, chromogenic substrates, chemiluminescent molecules, and enzymes.

11. The method of claim 1, further comprising the step of comparing the levels of MIF in the serum of the individual to the MIF levels of prostate cancer patients.

\* \* \* \* \*